(12) United States Patent
Phillips et al.

(10) Patent No.: US 7,317,937 B2
(45) Date of Patent: *Jan. 8, 2008

(54) METHOD AND APPARATUS FOR MONITORING CEREBRAL PHYSIOLOGY

(75) Inventors: Jeffrey Owen Phillips, Ashland, MO (US); Roger Eugene Huckfeldt, Columbia, MO (US)

(73) Assignee: Curators of the University of Missouri, Columbia, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/313,470

(22) Filed: Dec. 21, 2005

(65) Prior Publication Data

US 2006/0155177 A1 Jul. 13, 2006

Related U.S. Application Data

(63) Continuation of application No. 09/600,012, filed as application No. PCT/IB99/00088 on Jan. 7, 1999, now Pat. No. 7,020,505.

(30) Foreign Application Priority Data

Jan. 8, 1998 (GB) ................................. 9800370.0

(51) Int. Cl.
*A61B 5/00* (2006.01)
(52) U.S. Cl. ....................... 600/310; 600/361
(58) Field of Classification Search ................ 600/309, 600/310, 300, 361, 378; 604/19, 20, 21, 604/27, 28
See application file for complete search history.

(56) References Cited

U.S. PATENT DOCUMENTS

| | | | |
|---|---|---|---|
| RE31,879 E | 5/1985 | Lubbers et al. | |
| 4,830,849 A | 5/1989 | Osterholm | |
| 4,889,407 A * | 12/1989 | Markle et al. | ................ 385/12 |
| 4,903,707 A | 2/1990 | Knute et al. | |
| 4,904,237 A | 2/1990 | Janese | |
| 5,117,836 A | 6/1992 | Millar | |
| 5,257,338 A * | 10/1993 | Markle | ....................... 385/125 |
| 5,403,746 A | 4/1995 | Bentson et al. | |
| 5,531,776 A | 7/1996 | Ward et al. | |
| 5,579,774 A | 12/1996 | Miller et al. | |
| 5,704,352 A | 1/1998 | Tremblay et al. | |
| 5,830,188 A | 11/1998 | Abouleish | |
| 5,833,603 A | 11/1998 | Kovacs et al. | |
| 5,951,476 A | 9/1999 | Beach | |
| 6,049,727 A | 4/2000 | Crothall | |
| 7,020,505 B1 * | 3/2006 | Phillips et al. | .............. 600/310 |

(Continued)

OTHER PUBLICATIONS

Linda Pai, M.D. et al., MO Chapter Am. College of Surgeons, 30th Annual Prof Mtg, Jun. 13-15, 1997, "Continuous Evaluation of Cerebral Perfusion in Severe Brain Injury," p. 22.

(Continued)

*Primary Examiner*—Eric F Winakur
(74) *Attorney, Agent, or Firm*—Blackwell Sanders LLP

(57) ABSTRACT

A method and apparatus for predicting the outcome of head injury trauma by monitoring cerebrospinal fluid (CSF) characteristics, preferably by monitoring the pH of CSF. The apparatus includes a catheter with a wall section adapted to permit CSF to flow therein, and a sensor located within the catheter such that the CSF is permitted to flow adjacent the tip of the sensor.

5 Claims, 2 Drawing Sheets

OTHER PUBLICATIONS

Webster's New World Dictionary of American English, Webster's Now World Dictionaries, 3rd College Edition, p. 1011, undated.

Enevodsen, E.M. and F.T. Jensen, "Cerebrospinal fluid lactate and pH in patients with acute severe head injury,"0 Clin Neurol Neurosurg, 1977; 80(4), Abstract.

Venkatesh, B.R. et al., "The continuous measurement of cerebrospinal fluid gas tensions in critically ill neurosurgical patients: a prospective observational study," Intensive Care Med., 1999; 25(6), Abstract.

Offbeat Outline News at http://www.info.gov.hk/police/offbeat/archives/644/news3.thml (1997).

* cited by examiner

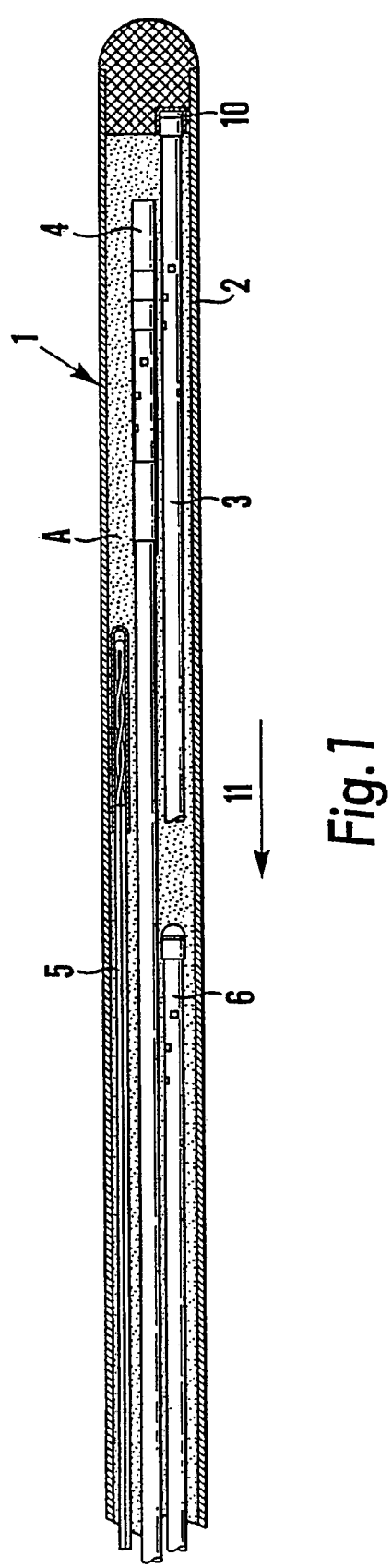
Fig.1
Fig.2

METHOD AND APPARATUS FOR MONITORING CEREBRAL PHYSIOLOGY

CROSS REFERENCE TO RELATED APPLICATIONS

This application is a continuation of and claims priority to U.S. application Ser. No. 09/600,012, filed Sep. 6, 2000 now U.S. Pat. No. 7,020,505, which is a 371 of PCT/IB99/00088 filed Jan. 7, 1999, which applications are hereby incorporated by reference to the extent permitted by law.

BRIEF SUMMARY OF THE INVENTION

This invention relates to a method and apparatus for monitoring the cerebral cellular environment, especially in patients who have sustained brain injury. In the event of medical incidents, such as severe trauma to the head, it is frequent practice to monitor the intracranial pressure (ICP) in a ventricle of the brain. An increase in ICP is thought to be indicative of secondary injury such as brain swelling, and it is known to be necessary to relieve pressure by draining cerebrospinal fluid (CSF) if a patient's ICP rises above a critical level. While a body of data exists in the management of intracranial hypertension there have been few investigations of the significance of other cerebral physiological parameters.

BRIEF SUMMARY OF THE INVENTION

The present invention is based on this observation that the pH of CSF is an indicator of the condition of a patient's brain after suffering head trauma and thus the likely outcome of medical treatment.

According to one aspect of the present invention there is provided a method of predicting the outcome of head trauma which comprises monitoring the pH of cerebrospinal fluid (CSF) and comparing the measured pH with a base line representing brain death.

In investigations which have been carried out by the present inventors, a pH sensor was inserted into a cerebral ventricle of a patient and the pH monitored by sequential measurements. Both the rate of change of pH and the absolute level of pH were measured on a continuous basis. While a rapid decrease of pH is a strong indicator of a poor survival prognosis, the absolute value of pH can be used directly to provide a guide to the patients' well being. In general, it has been found that stable levels of pH in the region of 7.15 to 7.25 suggest that the patient is likely to improve clinically, while significantly lower pH levels or continuously failing pH levels are a pointer to poor survival chances. In one case, a pH of about 7.05 correlated with brain stem death.

The present invention also includes apparatus for monitoring the pH and optionally other cerebral physiological parameters which comprises a lumen adapted for introduction through an opening in a skull of a living patient into a cerebral ventricle, said lumen having a pH sensor therein and permitting CSF to flow thereinto and over the sensor.

Preferably, the pH sensor contains a pH-sensitive colour change or fluorescent material and the colour change or fluorescence is measured optically by determining the absorption of a standard light beam.

The catheter containing the pH probe may be a single lumen and may also be used for removing samples of CSF fluid from the ventricle. Alternatively, a bitumen catheter may be employed in which the sensor is housed in one lumen and CSF is withdrawn from the other lumen. Removal of CSF may be desirable because of a perceived increase in ICP or may be removed prior to a detected increase in ICP because of a predicted deterioration in the patient's well being because of a fall in pH.

BRIEF DESCRIPTION OF THE SEVERAL VIEWS OF THE DRAWINGS

The invention is illustrated by reference to the accompanying drawings in which:—

FIG. 1 is a section through a tubular probe containing various sensors;

FIG. 2 is a part section through the probe;

DETAILED DESCRIPTION OF THE INVENTION

Figure 3A:
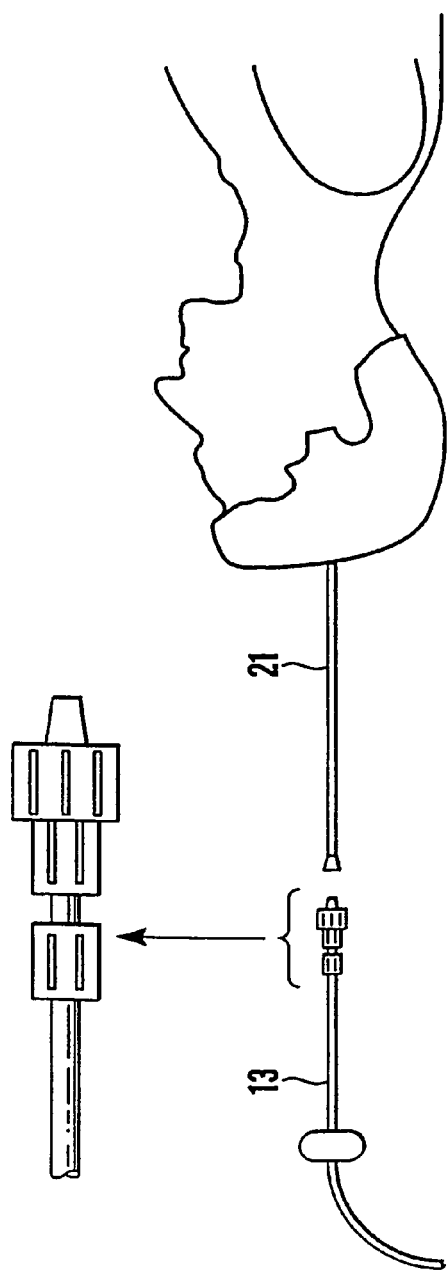
FIG. 3A is an enlarged view of the Luer lock.

Referring to the drawings the apparatus comprises a tubular probe (1) comprising a microporous sheath which permits the transfer of CSF into a gel (A) filling the probe. A number of sensors are housed within the tubular probe. One of these is a pH sensor (3). Sensor 3 comprises a length of optical fibre having a mirrored distal end 10 to reflect light back towards the proximal end 11, longitudinally of the optical fibre. Several holes (12) are laser drilled through the optical fibre in a number of random directions normal to the longitudinal axis of the fibre. These holes are filled with a gel containing a phenol red dye which undergoes a colour change with change in pH. A colour change over the pH range from about 6.8 to 7.8 is desirable. The colour shade of the phenol red indicator is determined by passing a light beam along the optical fibre and measuring the absorption spectrum of the reflected beam. After calibration, the absorption spectrum of the reflected beam gives a measure of the pH of the CSF.

As indicated in FIG. 1, the tubular probe may also include other sensors such as a $CO_2$ concentration sensor ($pCO_2$), 4, a partial oxygen pressure sensor ($pO_2$), 6, and a thermocouple 5.

Tubular probe 1 is introduced into a ventriculostomy catheter 21 which has a distal end having a foraminous wall to permit CSF to flow into and around the tip of the probe.

The catheter may be introduced into the patient's skull and retained in place with a tubular skull bolt, e.g. as shown in U.S. Pat. No. 4,903,707 (the contents of which are specifically incorporated herein by reference). Conveniently, the catheter is urged into the opening in the skull until expression of CSF indicates that the catheter tip has reached the cerebral ventricle.

The catheter 21 has a distal end into which the tip of the probe is positioned. In the Example illustrated, the catheter comprises a single lumen, e.g. of PVC or polypropylene. The catheter is connected via a Luer lock to an extension tube 13 which may incorporate a side port (not shown) for sampling CSF and monitoring ICP. The extension tube is further connected by optical fibres to a detection, monitoring and display equipment.

Figure 3B:
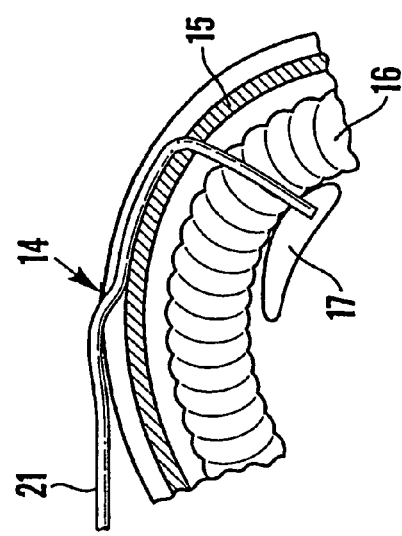
FIG. 3B is a partial section through the patient's head showing one method of introducing the lumen containing the pH sensor.

Apparatus which is commercially available for intravascular blood monitoring under the registered trade mark 'Paratrend' 7 (Diametrics Medical Ltd 5, Manor Court Yard, Hughendon Ave, High Wycombe, HP13 5RE, United Kingdom) may be adapted for monitoring the pH of CSF by providing means for holding the sensor lumen in place in the skull. This may involve a bolt as described in the above cited U.S. Pat. No. 4,903,707 or secured by other fixing means as indicated in FIG. 3B. Referring to this latter Figure it can be seen that the catheter 21 is fixed to the patient's head by securing means 14, passes under the scalp in contact with the skull 15 and then through an opening in the skull and brain 16 to reach a brain ventricle 17. The small, size and flexibility of the catheter (about 2-3 mm diameter) facilitates introduction of the catheter. The distal tip of the catheter is provided with holes to permit flow of CSF therethrough and around the tip of the probe which is also located within the cerebral ventricle.

EXAMPLE 16 patients admitted to hospital following brain trauma resulting in severe brain injury (GCS≦8) were included in the study. A 'Paratrend 7' sensor measuring pH, $pCO_2$ and $pO_2$ was advanced into a ventriculostomy. Sensor data was stored into a computer and transferred to a spreadsheet, pH, $pCO_2$, $pO_2$, 1CP, CPP, patent manipulation and outcome were monitored.

Six patients were excluded due to technical difficulties in obtaining and recording data early in the study.

Four patients were found to have initial pH in the range 7.15 to 7.22 but had progressive CSF acidemia over the next 24 to 48 hours. All progressed to herniation and brain death. Clinical evidence of brain death occurred as the pH approached 7.05.

Two patients were found to have a relative high initial CSF pH in the range 7.20-7.25. These values remained substantially constant and both patients remained vegetative.

In the remaining four patients initial pH was in the range 7.12 to 7.24 but increased over the following 48 hours. All displayed significant clinical recovery.

It was found that patient care activities and other known stressors were found to cause a rapid decrease in CSF pH which resolved shortly after the activity stopped. All negative changes in brain pH occurred significantly before elevations of ICP or change in CPP could be detected. This suggests that CSF pH is a more effective indicator of a patient's neurological condition since remedial action can be taken earlier. It was also noted that measurement of CSF pH provides a means for monitoring cerebral ischemia following blunt head trauma. Falling pH correlates to ongoing cellular injury and occurs well before increases in intracranial pressures.

The invention claimed is:

1. Apparatus for predicting the outcome of head trauma, the apparatus comprising:
    a pH probe for reception in a patient's brain ventricle;
    means for monitoring the pH of CSF over time;
    means for calculating the pH at the probe at sequential times;
    means for comparing the calculated pH values with stored values, wherein each stored value is correlated with an outcome of head trauma; and
    means for displaying and/or recording the comparison results.

2. A method of diagnosing or treating neurological injuries using the apparatus of claim 1, the method comprising:
    inserting the pH probe into a patient's brain ventricle;
    monitoring the pH of CSF over time;
    calculating the pH at the probe at sequential times;
    comparing the calculated pH values with the stored values; and
    displaying and/or recording the comparison results.

3. The apparatus of claim 1 wherein the stored values correspond with a rate of chance of CSF pH.

4. The apparatus of claim 3 wherein the stored values further correspond with absolute level of CSF pH.

5. The apparatus of claim 1, wherein the stored values correlate with outcomes within the initial 48 hours following blunt head trauma.

* * * * *